US012745903B2

(12) United States Patent

Avrahamov et al.

(10) Patent No.: US 12,745,903 B2
(45) Date of Patent: *Sep. 29, 2026

(54) AIR SPECULUM

(71) Applicant: Ivy Next Ltd., Caesarea Industrial Park (IL)

(72) Inventors: Ido Avrahamov, Rishpon (IL); Kfir Solomon, Zoran (IL); Sefi Shachrur, Pardes-Hana Karkur (IL)

(73) Assignee: Ivy Next Ltd., Caesarea Industrial Park (IL)

( * ) Notice: Subject to any disclaimer, the term of this patent is extended or adjusted under 35 U.S.C. 154(b) by 486 days.

This patent is subject to a terminal disclaimer.

(21) Appl. No.: 18/252,225

(22) PCT Filed: Nov. 14, 2021

(86) PCT No.: PCT/IB2021/060539

§ 371 (c)(1),
(2) Date: May 9, 2023

(87) PCT Pub. No.: WO2022/101864

PCT Pub. Date: May 19, 2022

(65) Prior Publication Data

US 2024/0008734 A1 Jan. 11, 2024

Related U.S. Application Data

(60) Provisional application No. 63/113,898, filed on Nov. 15, 2020.

(51) Int. Cl.

| | |
|---|---|
| *A61B 1/32* | (2006.01) |
| *A61B 1/00* | (2006.01) |

(Continued)

(52) U.S. Cl.
CPC ............ *A61B 1/32* (2013.01); *A61B 1/00142* (2013.01); *A61B 1/015* (2013.01); *A61B 1/05* (2013.01); *A61B 1/303* (2013.01)

(58) Field of Classification Search
CPC ....... A61B 1/015; A61B 1/05; A61B 1/00142; A61B 1/303
See application file for complete search history.

(56) References Cited

U.S. PATENT DOCUMENTS

2009/0099460 A1* 4/2009 Zuluaga ................ A61B 1/303 600/478
2010/0016668 A1* 1/2010 Gal ....................... A61B 1/303 600/135

(Continued)

FOREIGN PATENT DOCUMENTS

WO 2020/212923 10/2020
WO WO-2020212923 A1 * 10/2020 ............... A61B 1/32

OTHER PUBLICATIONS

PCT Search Report and Written Opinion PCT/IB2021/060539, Feb. 22, 2022.

*Primary Examiner* — Eduardo C Robert
*Assistant Examiner* — Anna V. Little
(74) *Attorney, Agent, or Firm* — AlphaPatent Associates Ltd.; Daniel J. Swirsky

(57) ABSTRACT

A speculum includes a speculum sheath formed with one or more fluid flow lumens in fluid communication with a pump and controller unit for introducing pressurized fluid into a vagina, a pressure sensor lumen in fluid communication with the pump and controller unit for measuring fluid pressure in the vagina, and a third lumen in which is disposed a viewing device, and a vaginal interface element that comprises flexible folds and is configured for pressing and sealing against a vagina.

10 Claims, 4 Drawing Sheets

(51) Int. Cl.
*A61B 1/015* (2006.01)
*A61B 1/05* (2006.01)
*A61B 1/303* (2006.01)

(56) References Cited

U.S. PATENT DOCUMENTS

| | | | | |
|---|---|---|---|---|
| 2012/0174675 | A1* | 7/2012 | Sasady | A61B 8/4209 73/632 |
| 2012/0289858 | A1* | 11/2012 | Ouyang | A61B 1/00101 600/562 |
| 2019/0254708 | A1* | 8/2019 | Wu | A61B 17/12099 |
| 2019/0298321 | A1* | 10/2019 | Intintoli | A61B 1/07 |
| 2020/0008840 | A1 | 1/2020 | Addis | |
| 2020/0187769 | A1* | 6/2020 | Rahimian | A61B 5/4306 |

* cited by examiner

AIR SPECULUM

FIELD OF THE INVENTION

The present invention relates to vaginal speculums and particularly to a vaginal speculum that uses pressurized air to maintain a passageway through the vagina, such as to gain access to the cervix or other anatomy.

BACKGROUND OF THE INVENTION

Vaginal speculums provide access to the vagina and cervix for physical examinations and for introducing surgical instruments, such as for collecting tissue samples or for introducing medications.

Inflatable vaginal speculums have been used to examine the vagina and cervix. However, prior art inflatable speculums require sealing the septum against the vaginal walls, such as with a watertight or airtight septum or plug placed at the distal end of the speculum. The seal is meant to prevent flow of fluid (water or air) from the vagina and at the same time permit pressurized flow into the vagina.

PCT Patent Application PCT/IB2020/053647 describes an air speculum. The speculum includes a speculum sheath formed with a first lumen which is in fluid communication with a pump and controller unit for introducing pressurized air into a vagina. A second lumen is in fluid communication with the pump and controller unit for measuring air pressure in the vagina. A third lumen is provided for a viewing device.

SUMMARY OF THE INVENTION

The present invention seeks to provide an air speculum with added features to those of the air speculum described in PCT Patent Application PCT/IB2020/053647, as described in detail below.

Most obstetrician/gynecologist visits involve visual inspection of the cervix or uterus, ultrasonic inspection, Pap smear sampling or other procedures. The speculum of the invention employs an extremely high-resolution wide-angle lens camera, illumination and a compact ultrasonic transducer in a hand-held device, enabling the doctor to get a full and clear image of the entire vaginal canal, cervix and surrounding tissues, plus the ability to obtain ultrasonic images, all in one complete device.

The camera's extreme high resolution enables digital zoom with no adverse effect on the image quality. The doctor can zoom in on areas that require thorough examination. A video of the examination can be recorded for later reference, as well as cross-clinic consultation.

The invention significantly reduces the overall time the patient needs to be inspected and increases the overall comfort and ease of inspection for both the patient and the physician.

There is thus provided in accordance with a non-limiting embodiment of the present invention a speculum including a speculum sheath formed with a first lumen which is in fluid communication with a pump and controller unit for introducing pressurized air into a vagina, a second lumen in fluid communication with the pump and controller unit for measuring air pressure in the vagina, and a third lumen in which is disposed a viewing device.

BRIEF DESCRIPTION OF THE DRAWINGS

The present invention will be understood and appreciated more fully from the following detailed description, taken in conjunction with the drawings in which.

DETAILED DESCRIPTION OF EMBODIMENTS

Figure 1:
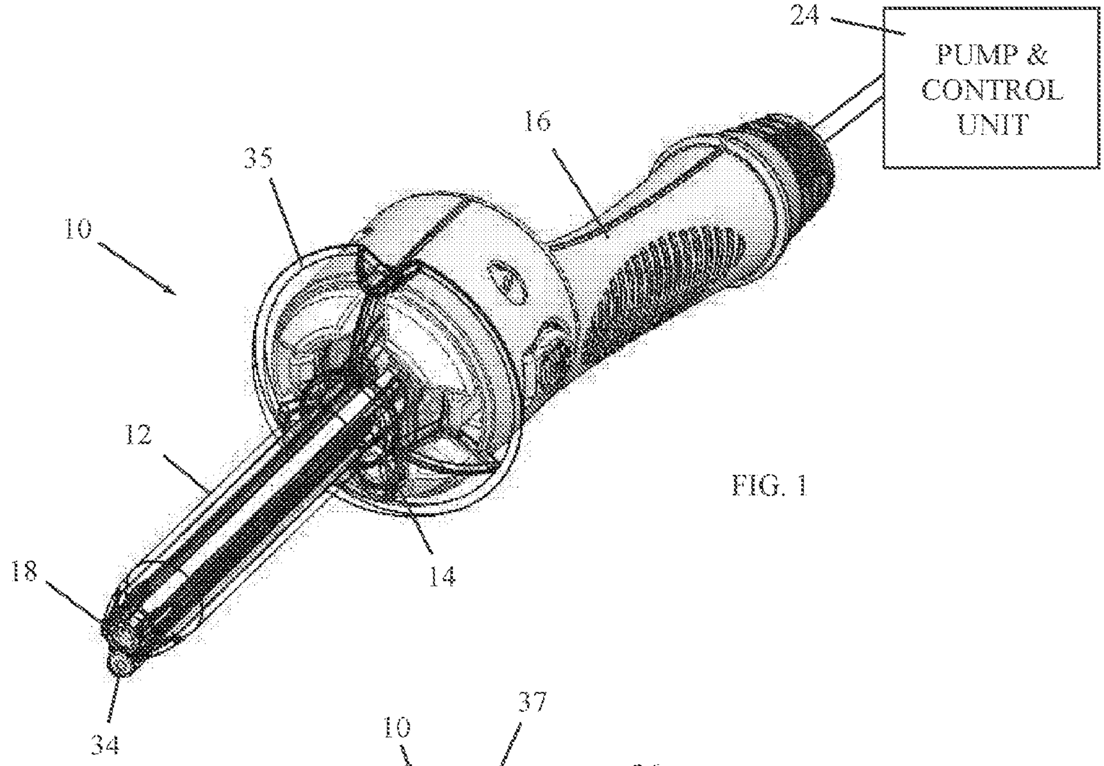
FIGS. 1, 2, and 3 are simplified pictorial illustrations of an air speculum, constructed and operative in accordance with a non-limiting embodiment of the present invention.
Figure 2:
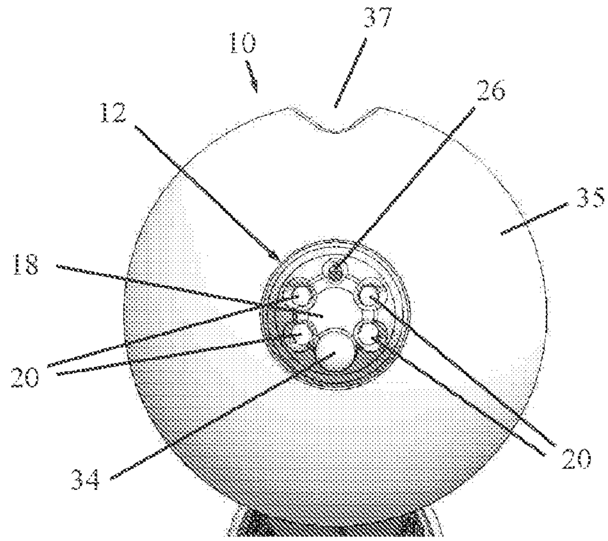
Figure 3:
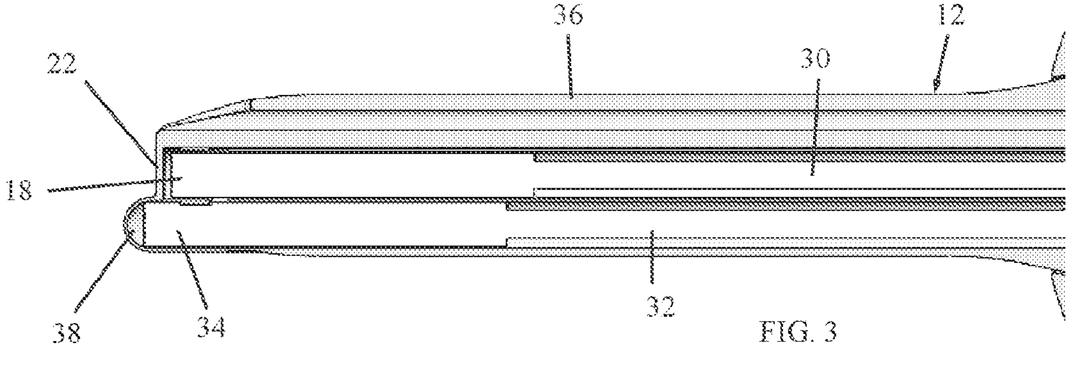

Reference is now made to FIGS. 1-3, which illustrate an air speculum 10, constructed and operative in accordance with a non-limiting embodiment of the present invention.

Speculum 10 includes a speculum sheath or shaft 12, which may be disposable, which couples with a light source 14, mounted on a handle 16. A viewing device (camera) 18 is arranged to pass into speculum sheath 12.

The speculum sheath 12 may be made of a medically-safe, rigid or flexible plastic (preferably transparent) and may be formed with several lumens. For example, one or more fluid flow lumens 20 (four are shown in the illustrated embodiment of FIG. 2, but the invention is not limited to this number) may be in fluid communication via fluid connectors and tubing (not shown) with a pump and controller unit 24 (as described in described in PCT Patent Application PCT/IB2020/053647), for introducing pressurized air or other fluids into the vagina. A pressure sensor lumen 26 may be in fluid communication (via a fluid connector and tubing, not shown) with pump and controller unit 24, for measuring air pressure in the vagina. A third lumen 30 is provided for placing therein viewing device 18. The light source 14 may be coupled to third lumen 30. The third lumen 30 (camera channel) may be closed at its distal end with an optically clear lens or window 22 to prevent any contact of tissues or fluids with viewing device 18 and avoid the need to sterilize viewing device 18.

The viewing device 18 may be, without limitation, a small diameter tube camera (1.6 mm) with a very wide lens (120°), good resolution and USB connection. The light source 14 may be one or more LEDs located on the handle 16. With light guides (e.g., optical fibers), the light is directed to the distal end of the device to illuminate the vaginal channel. With a wide lens and appropriate lighting, the user sees a well-illuminated picture of the vagina channel, and may move the device back and forth for viewing desired areas.

A fourth lumen 32 may be provided for an ultrasonic transducer 34. As seen in FIG. 2, the viewing device 18 may be positioned at the center of speculum sheath 12 and the ultrasonic transducer 34 may be positioned radially offset from the center of speculum sheath 12. As seen in FIG. 3, the ultrasonic transducer 34 may be positioned distal to the distal end of the viewing device 18.

Other lumens may be provided as working channels for passing therethrough tools, such as cutting tools, drug delivery tools, grasping tools, etc.

A disposable cover 36 may cover sheath 12. The disposable cover 36 may also act as a light-guide. The disposable cover 36 may be slipped over the viewing device 18 and ultrasonic transducer 34 to protect them from body fluids. An ultrasonic chamber 38 may be provided at the distal tip of the disposable cover 36. Chamber 38 may contain a breakable-seal sub-chamber with ultrasonic gel pre-loaded inside. An elastic (over-mold) cover may cover chamber 38.

The sizes, shapes and profiles of the air speculum and its lumens may be determined by different factors, such as but not limited to, a structure that minimizes or eliminates pain when inserting and using the device, and a structure that seals the entrance to the vagina as much as possible for efficient inflation and pressure measurement. For example, a vaginal interface element 35 (FIG. 1) may be provided at a proximal end of sheath 12 for pressing and sealing against the labia minora and/or labia majora of the vagina. The vaginal interface element 35 may be convex or concave, or have a cup-like shape, or any other suitable shape.

A notch 37 may be provided in vaginal interface element 35 to help align the parts during assembly and use.

The device may be, without limitation, approximately 6 mm in diameter. The fluid flow lumens 20 may be used to inflate the vaginal canal up to 20 mmHg, without limitation. The inflation fluid may be air, $CO_2$ or nitrogen, for example. The pressure sensor lumen 26 may be used to sense the real-time pressure in the vaginal tunnel to avoid pressure drops, and also may be used to as a pressure relief valve for safety. The pressure may be sensed by the control unit using PID (proportional integral derivative) control that operates in a control loop feedback for optimal safety and efficiency.

Figure 4A:
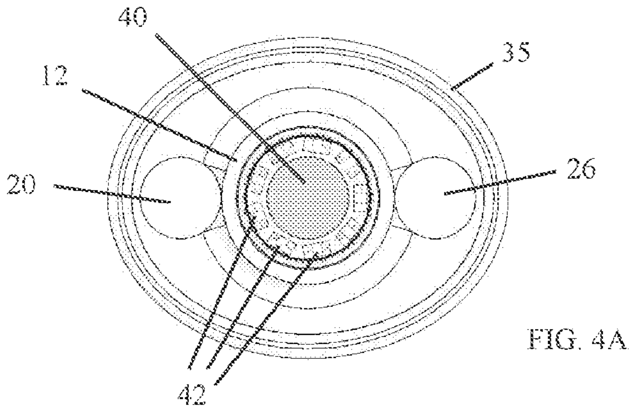
FIGS. 4A, 4B and 4C are simplified pictorial illustrations of an air speculum, constructed and operative in accordance with another non-limiting embodiment of the present invention.
Figure 4B:
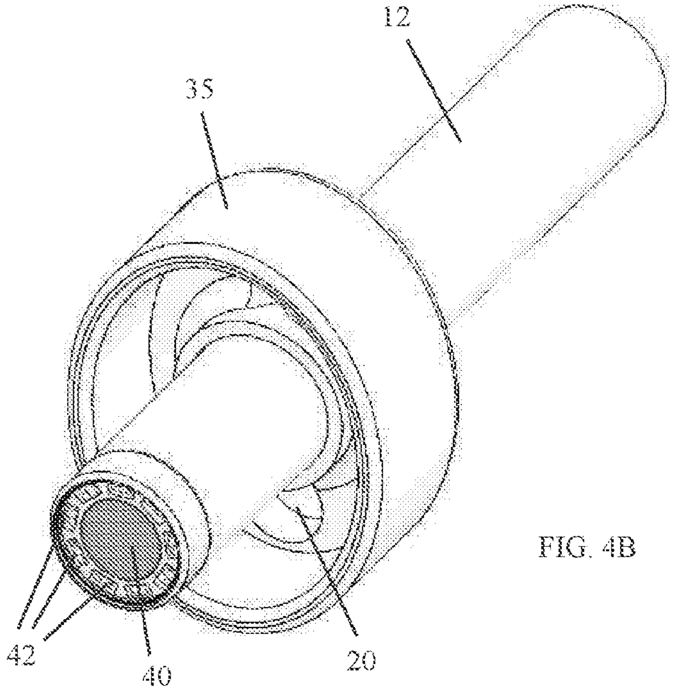
Figure 4C:
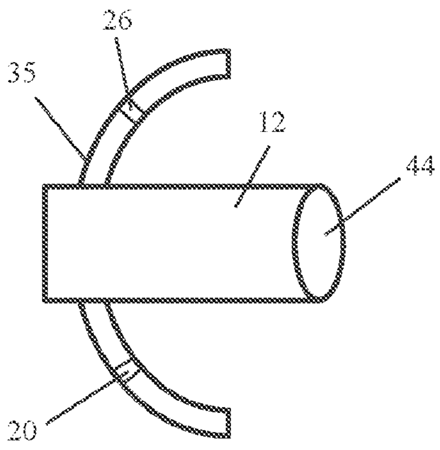

Reference is now made to FIGS. 4A-4C, which illustrates another viewing device 40, which may be used with any air speculum of the invention. Viewing device 40 may include a miniature digital camera (without limitation, diameter 15-20 mm) with zoom capability (without limitation, 5×, 10× or 15× zoom).

The digital controls for the camera zoom are conveniently located on the device handle (handle 16 of FIG. 1). The user can operate and record video single handedly, leaving the other hand for other essential clinic logistics.

In this embodiment, the light source 42, such as but not limited to, an array of LEDs, may be at the distal end of sheath 12 near the viewing device 40. As seen in FIG. 4C, the vaginal interface element 35 may be convex or concave, or have a cup-like shape, or any other suitable shape. The lumens 20 and 26 may pass through vaginal interface element 35 and may be tilted with respect to the longitudinal axis of sheath 12.

A magnifying lens 44 may be provided at the distal end of the viewing device.

Figure 5:
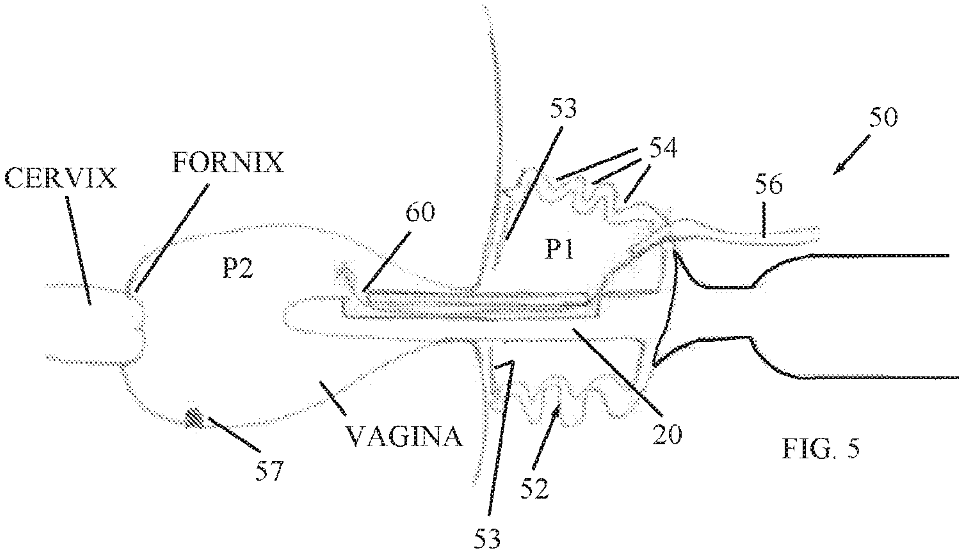
FIG. 5 is a simplified illustration of an air speculum, constructed and operative in accordance with another non-limiting embodiment of the present invention.

Reference is now made to FIG. 5, which illustrates an air speculum 50, constructed and operative in accordance with another non-limiting embodiment of the present invention. The air speculum 50 may include any of the features of air speculum 10 and viewing device 40 and like elements are designated by like reference numbers.

Air speculum 50 includes a vaginal interface element 52, which may include a soft, flexible cup with folds 54. The vaginal interface element 52 may include one or more pressure concentration elements 53 extending from the cup in the area where element 52 presses against the body. The vaginal interface element 52 may be shaped as a bellows, for example. FIG. 5 shows vaginal interface element 52 pressing against the labia minora and/or labia majora of the vagina so as to reduce and flow of material outwards. Pressurized air or other fluid (for example, from pump and controller unit 24, not shown in FIG. 5) may be introduced through a pressurized fluid delivery tube 56 that leads pressurized fluid through fluid flow lumen 20 past the inner volume of vaginal interface element 52 and through an exit port 60 on speculum shaft 12 into the vagina.

Figure 5A:
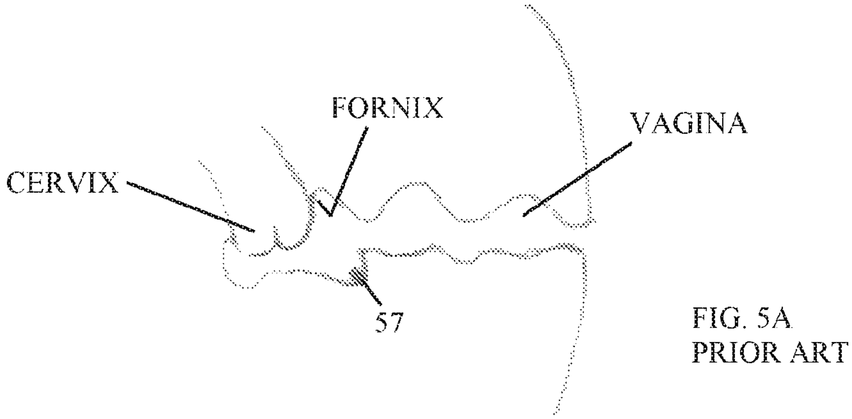
FIG. 5A PRIOR ART
FIG. 5A is a simplified illustration of the anatomy before inflation by means of the air speculum of FIG. 5.

The efficacy of the air speculum 50 can be appreciated by comparing FIG. 5 with FIG. 5A, which shows the anatomy before inflation by means of air speculum 50. In FIG. 5A, a polyp 57 may be located in the folds of the vagina, and not readily visible. The cervix is tilted with respect to the vagina and the fornix has a well-defined crease or fold. After inflation with air speculum 50, as seen in FIG. 5, the cervix is less tilted or not tilted at all with respect to the vagina and the fornix has flattened out. This greatly increases the visibility of the cervix and its accessibility for introducing instruments or substances. The polyp 57 is readily visible due to the wrinkles and folds being flattened by the inflation.

It is noted that with air speculum 50, the pressure in the inflated vagina up to the cervix (P2) is about equal to the pressure in the inner volume of vaginal interface element 52 (P1). This equalization of pressures reduces or eliminates any unwanted sounds that could be created by pressurized air escaping from the inflated vagina due to unequal pressurization of the vagina.

The vaginal interface element 52 is soft and gentle to the patient and also reduces the force required by the physician to press against the vagina. This also enables the physician to move freely to view objects in the vagina without losing any substantial flow of materials outwards.

The pressure source for inflating the vagina may be, without limitation, a centrifugal pump or a blower that operates at low pressure but with a high fluid delivery. As with other embodiments, the pressure sensor lumen 26 (not shown here, but shown in FIGS. 2 and 4A) may be used as a static tube with no flow, to sense the real-time pressure in the vaginal tunnel to avoid pressure drops, and also may be used to as a pressure relief valve for safety that operates in a control loop with the pump and controller unit for measuring fluid pressure in the vagina and for cutting off pressure to prevent over-pressurization. Without limitation, the pressure for inflating the vagina may start at 12 mbar and increase gradually or incrementally to a maximum of 50 mbar.

Figure 6A:
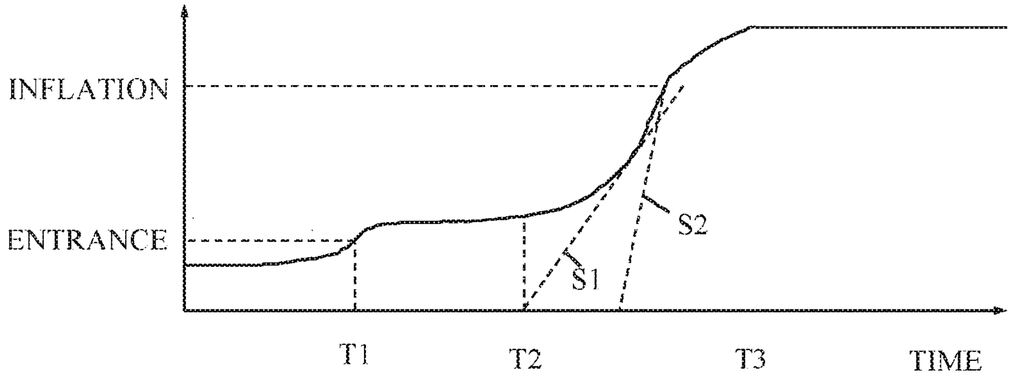
FIG. 6A is a graphical illustration of pressure measurement which can be used to monitor inflation of the vagina with the air speculum of the invention.
Figure 6B:
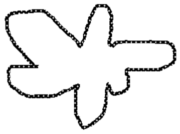
FIGS. 6B, 6C, and 6D are simplified illustrations of three different stages of inflation of the vagina.
Figure 6C:
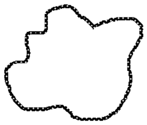
Figure 6D:
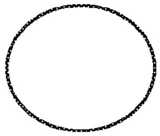

Reference is now made to FIG. 6A, which illustrates a graph of pressure measurement which can be used to monitor inflation of the vagina with the air speculum of the invention, and to FIGS. 6B, 6C, and 6D, which illustrate three different stages of inflation of the vagina.

The initial pressure seen in the graph of FIG. 6A may be constant at first before entering the vaginal cavity, but after time T1, increases slightly, which indicates the pressurized fluid has entered the vaginal cavity. FIG. 6B shows the vaginal cross-section before inflation. The pressure may increase and then become somewhat constant up to time T2, which indicates the vaginal cavity has been filled (corresponding to FIG. 6C). At this point in time, the pressure starts to increase due to the opposition of the vaginal wall from being inflated. The increase in pressure may have two stages: a first stage with a first slope S 1, which indicates a first rate of increase (corresponding to FIG. 6C), and a second stage with a second slope 52, which indicates a second rate of increase, which is greater than the first rate of increase die to the extra pressure needed to flatten out wrinkles and folds (corresponding to FIG. 6D). Starting at a time T3, the desired pressure may be maintained for the duration of the examination of the patient. By monitoring the pressure measurement, one can monitor the inflation of the vagina.

Figure 7A:
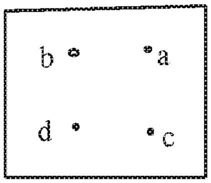
FIGS. 7A and 7B are illustrations of another method of monitoring inflation of the vagina with the air speculum of the invention, using image processing to indicate the stages of inflation.
Figure 7B:
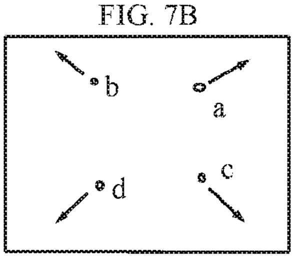

Reference is now made to FIGS. 7A and 7B, which illustrates another method of monitoring inflation of the vagina with the air speculum of the invention. This method uses image processing to indicate the stages of inflation. The method may identify initial positions of different points a, b, c, and d in an image of the vagina as seen in FIG. 7A (the images being captured by the camera or ultrasound described above, or by other imaging devices). Upon inflation of the vagina, these points move away from each other, as seen in FIG. 7B, and the change in position can be calibrated to determine the stages of inflation.

What is claimed is:

1. A speculum comprising:

a speculum sheath formed with one or more fluid flow lumens in fluid communication with a pump and controller unit for introducing pressurized fluid into a vagina, a pressure sensor lumen in fluid communication with said pump and controller unit for measuring fluid pressure in the vagina, and a third lumen in which is disposed a viewing device; and a vaginal interface element that comprises flexible folds and is configured for pressing and sealing against a vagina.

2. The speculum according to claim 1, wherein said pump and controller unit is capable of introducing the pressurized fluid into the vagina, so that pressure in the vagina equals pressure in an inner volume of said vaginal interface element.

3. The speculum according to claim 1, further comprising an ultrasonic transducer disposed in said speculum sheath.

4. The speculum according to claim 3, wherein said ultrasonic transducer is disposed in a fourth lumen in said speculum sheath.

5. The speculum according to claim 3, wherein said viewing device is positioned at a center of said speculum sheath and said ultrasonic transducer is positioned radially offset from the center of said speculum sheath.

6. The speculum according to claim 3, wherein said ultrasonic transducer is positioned distal to a distal end of said viewing device.

7. The speculum according to claim 1, wherein a disposable cover covers said speculum sheath.

8. The speculum according to claim 7, wherein said disposable cover comprises a light-guide.

9. The speculum according to claim 7, wherein an ultrasonic chamber is provided at a distal tip of said disposable cover, said ultrasonic chamber comprising a breakable-seal sub-chamber with an ultrasonic gel therein.

10. The speculum according to claim 1, wherein said viewing device comprises a camera with zooming capability.

* * * * *